(12) United States Patent
Wilcox et al.

(10) Patent No.: US 8,075,565 B2
(45) Date of Patent: Dec. 13, 2011

(54) SURGICAL INSTRUMENTS FOR DELIVERING FORCES TO BONY STRUCTURES

(75) Inventors: Bryan S. Wilcox, Collierville, TN (US); Jesse Gabriel Moore, Memphis, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 465 days.

(21) Appl. No.: 12/264,957

(22) Filed: Nov. 5, 2008

(65) Prior Publication Data

US 2010/0114182 A1    May 6, 2010

(51) Int. Cl.
*A61B 17/00* (2006.01)
(52) U.S. Cl. ........ 606/86 A; 606/105; 606/279; 606/916
(58) Field of Classification Search .................. 606/914, 606/916, 86 A, 103, 208, 105, 104, 90, 86 R, 606/250–279, 246–249, 205–207, 209; 81/393–394, 81/405, 407, 408, 462, 451, 436
See application file for complete search history.

(56) References Cited

U.S. PATENT DOCUMENTS

| 49,424 | A | | 8/1865 | Linsey |
|---|---|---|---|---|
| 111,907 | A | | 7/1938 | Rue |
| 2,460,470 | A | * | 2/1949 | Rogers ........................ 606/86 R |
| 5,910,141 | A | | 6/1999 | Morrison et al. |
| 7,686,814 | B2 | * | 3/2010 | Lim et al. ...................... 606/105 |
| 7,811,288 | B2 | * | 10/2010 | Jones et al. ................. 606/86 A |
| 2003/0236529 | A1 | | 12/2003 | Shluzas et al. |
| 2004/0024411 | A1 | | 2/2004 | Newton et al. |
| 2005/0010220 | A1 | * | 1/2005 | Casutt et al. ..................... 606/61 |
| 2005/0131408 | A1 | * | 6/2005 | Sicvol et al. .................... 606/61 |
| 2005/0245928 | A1 | * | 11/2005 | Colleran et al. ................ 606/61 |
| 2006/0009777 | A1 | | 1/2006 | Lim et al. |
| 2006/0122597 | A1 | * | 6/2006 | Jones et al. ..................... 606/61 |
| 2008/0119862 | A1 | * | 5/2008 | Wicker et al. ................... 606/99 |
| 2009/0054902 | A1 | * | 2/2009 | Mickiewicz et al. ......... 606/103 |
| 2010/0004695 | A1 | * | 1/2010 | Stad et al. ................... 606/86 A |
| 2011/0172674 | A1 | * | 7/2011 | Bankoski et al. ............. 606/104 |
| 2011/0184469 | A1 | * | 7/2011 | Ballard et al. ................ 606/279 |

* cited by examiner

*Primary Examiner* — Todd Manahan
*Assistant Examiner* — Jan Christopher Merene

(57) ABSTRACT

Spinal surgical systems, instruments and methods include a surgical instrument with a first member mountable to a first vertebra and a second member mountable to a second vertebra. The first and second members are coupled to one another with a coupling mechanism that allows translation of the first and second members relative to another along a predetermined path. The coupling mechanism also provides a pivot axis about which the first and second members are manipulated relative to one another to deliver forces to the first and second vertebrae.

19 Claims, 3 Drawing Sheets

SURGICAL INSTRUMENTS FOR DELIVERING FORCES TO BONY STRUCTURES

BACKGROUND

Surgical procedures for placing orthopedic devices such as spinal rods, plates, tethers, staples and other implants along the spinal column are becoming less invasive. However, the decrease in space available in the approach to the surgical site and at the surgical site for handling and manipulating of the implants and/or bony structures to which the implants are to be engaged increases the difficulty in maneuvering, maintaining and finally positioning of the implants and bone structures during the procedure. Furthermore, the ability to manipulate the vertebrae of the spinal column by applying compression, distraction, reduction and other forces is hindered by the small size of the surgical approach to the vertebrae, the complexity and size of the footprint of the instruments involved in delivering the compression forces, the vital anatomical structures adjacent the surgical site, and other factors. The ability to deliver forces to manipulate vertebrae through a minimally invasive access portal while minimizing the complexity in using and handling the instruments employed in the procedure would be desirable.

SUMMARY

Spinal surgical systems, instruments and methods include a surgical instrument with a first member mountable to a first vertebra and a second member mountable to a second vertebra. The first and second members are movable relative to one another to a desired relative position and orientation while coupled to one another. The first and second members are manipulated relative to one another while remaining coupled to one another to deliver forces to the first and second vertebrae.

According to one aspect, a spinal surgical instrument comprises: a first member engageable to a first vertebra, the first member including an elongated body extending along a first longitudinal axis between a proximal end and a distal end. The body of the first member includes a proximal portion extending distally from the proximal end to an intermediate end surface, a pair of arms extending distally from the intermediate end surface to a foot at the distal end of the body with the pair of arms defining an elongated opening between the foot and intermediate end surface. The pair of arms further each includes a mounting portion with at least one coupling mechanism mounted to the mounting portions. The foot includes an end wall extending between the pair of arms and a pair of toes extending distally from the end wall to a distal portion oriented transversely to the proximal portion of the toes. The instrument further comprises a second member including an elongated shaft defining a central passage along a second longitudinal axis that extends between a proximal end and a distal end of the shaft. The distal end of the second member is engageable to a second vertebra. The second member is positioned through the opening between the arms of the first member. The second member also includes first and second elongated slots extending along the second longitudinal axis on opposite sides of the shaft with the slots opening into the passage at a location between the proximal and distal ends of the shaft. The at least one coupling mechanism on the mounting portions of the first member is slidingly received in the slots of the second member so that the at least coupling mechanism of the first member is movable along the first and second slots of the second member to select a desired position of the first member along the second longitudinal axis. The at least one coupling mechanism further provides a pivot axis about which the first and second members pivot relative to one another.

According to another aspect, a spinal surgical instrument comprises a first member including an elongated body extending along a first longitudinal axis between a proximal end and a distal end, the body including a proximal portion extending from the proximal end that defines a handle portion and a distal portion that includes a pair of arms spaced from one another on opposite sides of an opening between the pair of arms. The pair of arms extends distally from the handle portion to a foot at the distal end of the first member with the opening extending between the foot and the proximal handle portion. The pair of arms further includes at least one coupling mechanism mounted thereto. The instrument also includes a second member including an elongated shaft that extends along a second longitudinal axis and defines a passage extending between and opening at a proximal end and a distal end of the elongated shaft. The second member is movably received in the opening of the first member with the elongated shaft including opposite slots elongated along the second longitudinal axis for receiving the at least one coupling mechanism of the first member. The at least one coupling mechanism maintains a pivotal connection between the first and second members while the at least one coupling mechanism is movable along the slots in the direction of the second longitudinal axis of the second member to adjust a relative positioning of the first member along the longitudinal axis of the second member.

In another aspect, a spinal surgical method, comprises: positioning a minimally invasive access portal in a patient to provide a protected pathway to at least one vertebra; engaging first and second anchors to the at least one vertebra; positioning a distal end of a first member and a distal end of a second member into the portal, the first member including an elongated body extending from the distal end of the first member to an opposite proximal end of the first member with the first member defining an opening extending through the body thereof between the proximal and distal ends, wherein the second member extends from the distal end thereof through the opening to an opposite proximal end; axially translating the first member along a predetermined path defined by the second member to select a position of the first member along the second member to mount the distal end of the first member to the first anchor and the distal end of the second member to the second anchor; and pivoting the first member and the second member about a pivot axis defined at the position to move the distal ends of the first and second members relative to one another to deliver a force to the first and second anchors with the first and second members These and other aspects are discussed further below.

DESCRIPTION OF THE ILLUSTRATED EMBODIMENTS

Figure 1:
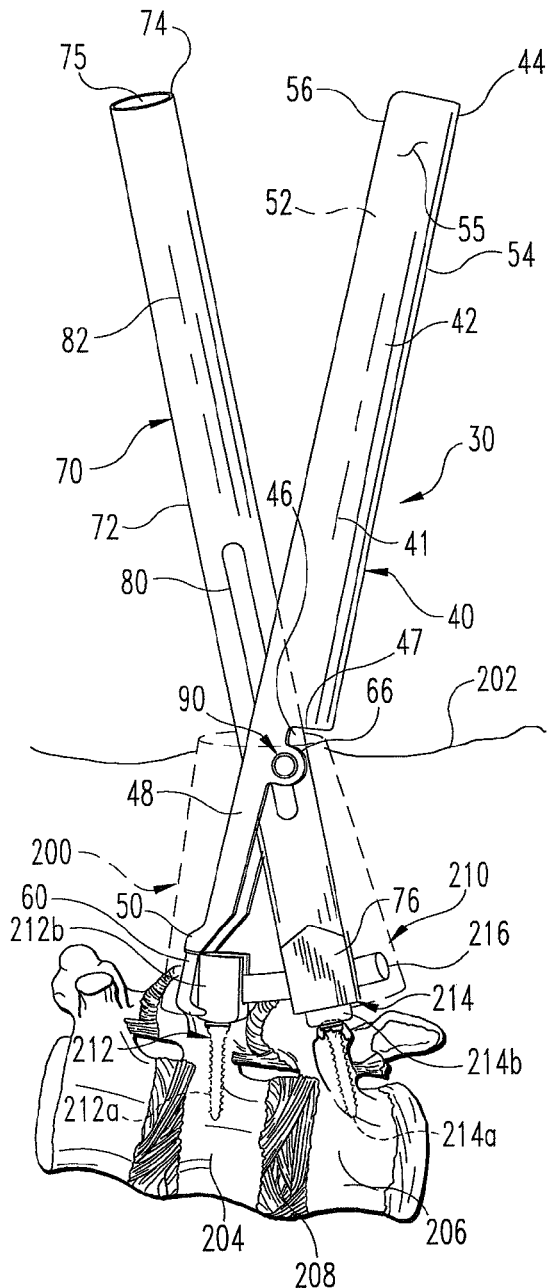
FIG. 1 is a perspective view of an instrument system positioned through an access portal and mounted to a construct engaged to the spinal column.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

There are provided systems and surgical instruments for applying forces to vertebrae of the spinal column or other bones that include a first elongated member mountable to a first vertebra and a second elongated member mountable to a second vertebra independently of the first member. In this arrangement the first and second members are movable relative to one another along a predetermined path for engagement to anchors or bony structure at the surgical site. The first member includes an elongated body having an intermediate opening to receive an elongated shaft of the second member therethrough so the first and second members can be nested or cross one another when mounted to the vertebrae. The desired relative spacing and elevations of the distal ends of the first and second members can be adjusted along the predetermined path to provide optimal engagement with the vertebrae. Once the desired positioning of the distal ends of the first and second members is obtained, the first and second members are pivotal relative to one another about a pivot axis located on the pre-determined path to manipulate the anchors and/or the bony structures to which the anchors are engaged. The arrangement eliminates the fiddle factor that would be present if the first and second members were not coupled to one another, while maintaining the ability to vary the location of the pivot axis along the predetermined path. The surgical instrument is operable by the surgeon to apply forces to the vertebrae or other bony structure by moving the proximal ends of the first and second members relative to one another, which moves the distal ends of the first and second members relative to one another about the pivot axis to manipulate the vertebrae and/or bony structures to which the distal ends are mounted.

In another embodiment, a surgical instrument includes an elongated first member and an elongated second member, which are positionable through a minimally invasive access portal in operative approach to at least one vertebra or other bony structure. The first and second members are mountable to the at least one vertebra, and are coupled to one another with a coupling mechanism so that the first member is translatable along the axis of the second member while the first and second members are coupled to one another. The first and second members are also pivotal relative to one another about the coupling mechanism in order to manipulate anchors and/or bony structures engaged at the distal ends of the first and second members.

In another embodiment, the distal end of the surgical instrument is mounted to one or more anchors engaged to one or more vertebrae. A connecting member extends between the first and second anchors, and is secured between the anchors when the desired forces are applied to the bony structure engaged to the anchors. The connecting member can be a rod, plate, staple, flexible member or other suitable device positionable to extend between vertebrae for engagement to the vertebrae and maintain the forces on the bony structure achieved with the surgical instrument.

The surgical instrument can be manipulated to deliver compression forces to the bony structure by moving proximal ends of the first and second members toward one another, thus moving the distal ends of the first and second members toward one another. Alternatively, distraction forces can be applied to the bony structure by moving the proximal ends, and thus the distal ends, of the first and second members away from one another. The forces can displace one or more portions of the bony structure, and/or apply forces to implants positioned between the bony structures. The forces are maintained post-operatively with an implant system extending between the bony structures.

The surgical instrument can be employed in minimally invasive systems that provide a minimally invasive approach to one or more vertebrae or other bony structure. In one embodiment, the minimally invasive approach is provided by a tubular retractor inserted through the tissue to provide a protected passageway to first and second anchors. In a further embodiment, the tubular retractor is expandable to increase the size of the working space adjacent the first and second anchors relative to the size of the incision or opening through which the retractor is inserted. In another embodiment, the approach is provided by one or more retractor blades inserted through the incision to provide a pathway to the first and second vertebrae. In another embodiment, the minimally invasive systems are employed directly through tissue through one or more micro-incisions. In another embodiment, the bony structure is exposed in a non-minimally invasive open surgical technique and the surgical instrument is employed through the open approach to deliver forces to the bony structures.

The bony structure with which the surgical instrument can be employed include a single vertebra, first and second adjacent vertebrae of the spinal column separated by a disc space, or vertebrae separated from one another by one or more intervening vertebrae. The approach to the spinal column can be posterior, lateral, oblique, postero-lateral, or any other suitable approach into the body of the patient. The first and second vertebrae can be located along any one or combination of regions of the spinal column, including the cervical, thoracic, lumbar and sacral regions. In other procedures, bony structures other than those associated with the spinal column of the body are contemplated.

Referring to FIG. 1, there is shown a minimally invasive access portal 200 positioned through skin and tissue 202. Access portal 200 provides a pathway to the spinal column, including first vertebra 204 and second vertebra 206 having a spinal disc space 208 therebetween. In the illustrated embodiment, access portal 200 is an expandable tubular retractor such as is described in U.S. Patent Application Publication No. 2003/0191371 A1, which is incorporated herein by reference. The expandable tubular retractor provides a portal that defines a protected passageway to the spinal column. The tubular retractor includes a first insertion configuration in which the retractor is cylindrical and is movable in situ to a second configuration in which the distal end of the retractor is enlarged to form a proximally tapered working channel between the distal and proximal ends of the retractor. However, as discussed above, any suitable instrument, technique, or retractor for accessing the spinal column is contemplated. In addition, vertebrae 204, 206 need not be directly adjacent vertebrae, and can be separated by one or more other vertebrae, or can be a single vertebra or other bony structure.

In FIG. 1 a construct 210 is engaged to vertebrae 204, 206 and extends therebetween. In the illustrated embodiment of FIG. 1, construct includes a first anchor 212 engaged to first vertebra 204, a second anchor 214 engaged to second vertebra 206, and a connecting member 216 extending between first and second anchors 212, 214. Anchors 212, 214 can be multiaxial type screws with a first portion 212a, 214a, respectively, including a screw member threadingly engageable to the bony structure of the respective vertebra, and a second receiver portion 212b, 214b with a receiver member pivotally mounted to an enlarged head of the respective first portions 212a, 214a. Connecting member 216 is an elongated rod received in passages of the receiver portions 212b, 214b of the anchors 212, 214. Connecting member 216 can be secured in or on the receiver portions 212b, 214b with an engaging element 218 (FIG. 6) that is engaged to respective ones of the receiver portions 212b, 214b to firmly seat connecting member 216 against a bottom surface of the receiver member or around a post or shaft of the respective anchors 212, 214.

Other forms for construct 210 are contemplated. For example, anchors 212, 214 can be uni-axial screws, bolts, hooks, posted screws, fixed angle screws, or other suitable structure including a first portion for engaging one or more vertebrae and a second portion for engaging the connecting member. Connecting member 216 can be a plate, strut, tether, staple, spacer or other suitable device for extending between two or more anchors. Furthermore, construct 210 can be arranged to extend between more than two vertebrae, or can be engaged to three or more anchors. Engaging element 218 can be a set screw, cap, or other device that engages connecting member 216 to anchors 212, 214.

FIGS. 1, 3, 4 and 6 show a surgical instrument 30 that is mountable to vertebrae 204, 206 and manipulatable relative thereto to deliver a force between vertebrae 204, 206. When the desired force has been applied, construct 210 is secured between vertebrae 204, 206 to maintain the force post-operatively and/or to maintain an adjusted position of the vertebrae achieved through application of the force. In the illustrated embodiment, surgical instrument 30 is mountable to anchors 212, 214 engaged to respective ones of the vertebrae 204, 206. It is also contemplated that surgical instrument 30 can be mounted directly to vertebrae 204, 206; or mounted to a secondary fastener or device engaged to vertebrae 204, 206 which does not form a part of the construct 210.

Surgical instrument 30 includes a first member 40 mountable to first vertebra 204. First member 40 includes an elongated body 42 extending along a longitudinal axis 41 between a proximal end 44 and a distal end 50. Body 42 includes a proximal handle portion 54 extending distally from proximal end 44 to an intermediate opening 46 having a proximal end at intermediate surface 47. A pair of arms 48 extends distally from intermediate surface 47 of body 42 and along the opposite sides of opening 46 located between arms 48. Arms 48 include a respective one of the mounting portions 66, 68 projecting outwardly therefrom. A foot 60 is provided at the distal ends of arms 48, and foot 60 includes a proximal wall 61 that extends between and connects arms 48 at the distal ends of arms 48, as shown further in FIG. 6. Foot 60 is offset laterally from a distally extending projection of arms 48 in order to facilitate engagement of foot 60 with receiver portion 212b, as discussed further below.

The distal end of foot 60 includes a pair of toes 64 each including a first portion 64a extending distally from opposite sides of wall 61. First portions 64a are separated by a space 62 so that when foot 60 is positioned against receiver portion 212b of anchor 212, connecting member 216 can extend into or through space 62 where it exits receiving portion 212b of anchor 212. First portions 64a extend along and abut the adjacent sides of receiver portion 212b of anchor 212. The first portions 64a each extend to a distal portion 64b that are also separated from one another and are oriented transversely to the respective first portion 64a to extend along the distal side of receiver portion 212b of anchor 212 and also on opposite sides of bone engaging first portion 212a. Toes 64 provide a firm grip on anchor 212 and prevent first member 40 from slipping off of receiver portion 212b of anchor 212 as first member 40 and receiver portion 212b are being manipulated with instrument 30. Furthermore, the shapes of the surfaces of toes 64 and receiver portion 212b are complementary to one another so that toes 64 encapsulate receiver portion 212b and provide a non-random orientation of receiver portion 212b relative to foot 60 and first member 40. Thus, receiver portion 212b rotates and/or pivots relative to bone engaging first portion 212a as first member 40 is rotated and pivoted. This arrangement maintains the passage of receiver portion 212b in a perpendicular or aligned normalized orientation relative to connecting member 216 to receive connecting member 216 through receiver portion 212b as connecting member 216 extends from second anchor 214. Furthermore, wall 61 can project laterally from toes 64 toward the distally extending projections of arms 48 to extend along the proximal side of receiver portion 212b to further assist in maintaining receiver portion 212b in its predetermined orientation relative to foot 60.

Figures 5, 6:
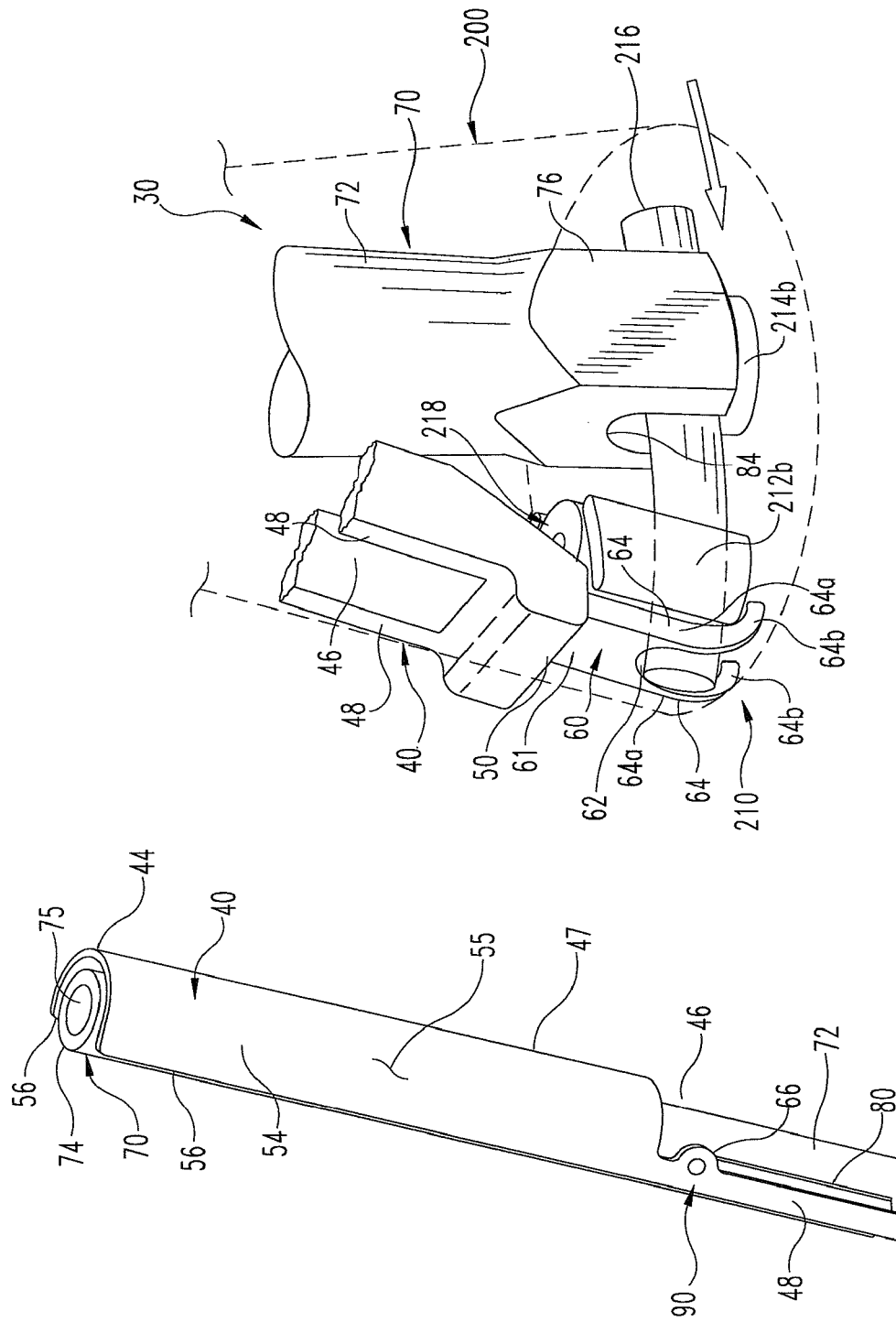
FIG. 5 is a perspective view showing proximal handles of the instrument system with the handle portion of the second member received in a channel of the handle portion of the first member.
FIG. 6 is a perspective view showing engagement of the distal portions of the first and second members with first and second anchors after applying a force between the first and second anchors with the first and second members.

Body 42 further includes opposing sidewalls 56 extending along at least proximal handle portion 54. A channel 52 extends between sidewalls 56. Channel 52 includes a U-shape formed by a concavely curved surface sized to receive elongated shaft 72 of second member 70 therein as shown in FIG. 5; however, other shapes are also contemplated, including non-curved shapes. Body 42 includes an outer surface 55 opposite channel 52 having a convex curvature to facilitate gripping of handle portion 54. Outer surface 55 can also include grip-enhancing features such as knurling, indentations, protrusions or the like.

Surgical instrument 30 further includes a second member 70 nestably positionable relative to and through opening 46 of first member 40 for mounting to second vertebra 206. Second member 70 includes an elongated shaft 72 having a tubular form with a circular or non-circular cross-section extending along a longitudinal axis 82 between a proximal end 74 and a distal engaging member 76. Elongated shaft 72 defines a passage 75 extending therethrough opening distally at engaging member 76 and proximally at the proximal end of shaft 72. Shaft 72 further includes elongated first and second slots 80, 81 on opposite sides thereof. Slots 80, 81 extend through the wall of shaft 72 and open into passage 75.

Passage 75 includes a distally oriented opening in engaging member 76 that is sized and structured to slip proximally over the receiver portion 214b of anchor 214 when it is engaged thereto, as further shown in FIG. 6. The outer side of engaging member 76 can be arranged in a non-circular configuration relative to the outer surface of shaft 72 to facilitate formation of the distal opening in engaging member 76 that is configured to extend about the receiver portion 214*b*. When engaging member 76 is positioned about receiver portion 214*b*, a firm interfit is provided therewith so that second member 70 can function as a counter-torque to prevent receiver portion 214*b* from pivoting or turning during the procedure. The distal end of engaging member 76 includes a distally-oriented and proximally extending recess 84 therein to receive connecting member 216 when engaging member 76 is fully seated on the receiver portion 214*b* of anchor 214, as shown in FIG. 6. The interface between engaging member 76 and receiver portion 214*b* of anchor 214 can be configured so that second member 70 cannot rotate relative to the receiver portion 214*b*, allowing the alignment of receiver portion 214*b* in the patient to be maintained during the procedure by controlling the positioning of second member 70 at the proximal end of shaft 72.

Figure 2A:
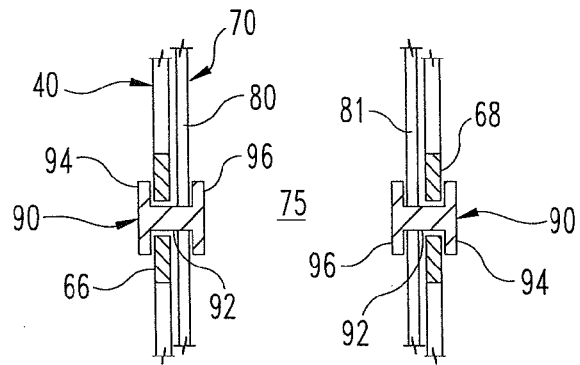
FIG. 2A is a section view of the coupling mechanism of the instrument system of FIG. 1.

Second member 70 extending through opening 46 of first member 40 and first member 40 is coupled to slots 80, 81 of second member 70 with at least one coupling mechanism 90. One embodiment of coupling mechanism 90 is shown in further detail in FIG. 2A. In the illustrated embodiment, two coupling mechanisms 90 are provided at each side of first member 40 in order to couple it to respective ones of the slots 80, 81. Each coupling mechanism 90 includes a linking member 92 extending through a respective one of the slots 80, 81 of second member 70 and a hole of the adjacent mounting portion 66, 68 of first member 40. Each coupling mechanism 90 also includes a first end member 94 at one end of linking member 92 located adjacent to the respective mounting portion 66, 68, and an opposite second end member 96 at the opposite end of linking member 92 adjacent to the inner wall surface of second member 70 along passage 75 adjacent to the respective slot 80, 81. End members 94, 96 project outwardly from linking member 92 to abut or lie in close proximity to the adjacent portions of first and second members 40, 70 and prevent linking member 92 from being pulled through slots 80, 81 and the holes of mounting portions 66, 68 through which linking members 92 extend. End members 96 in passage 75 maintain a low profile against the inner surface of shaft 72 so passage 75 remains substantially unobstructed to allow insertion of engaging element 218 through passage 75 to secure connecting member 216 to anchor 214, as discussed further below. First and second members 40, 70 are pivotal about linking members 92. Furthermore, linking members 92 are translatable along the respective slots 80, 81 to move first member 40 along the longitudinal axis of second member 70 along a predetermined path defined by slots 80, 81.

Figure 3:
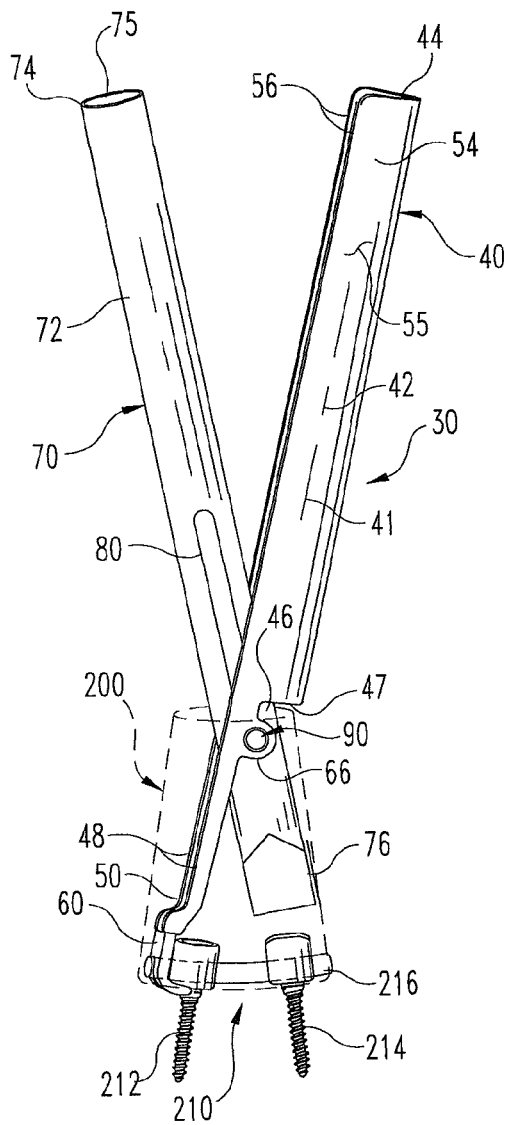
FIG. 3 is a view of the portal, construct and instrument system of FIG. 1 with a first member of the instrument system mounted to an anchor and the second member of the instrument system displaced proximally from its FIG. 1 position.

Coupling mechanism 90 allows engaging member 76 and shaft 72 to be adjusted in elevation relative to foot 60 of first member 40 to secure engaging member 76 to second anchor 214. For example, as shown in FIG. 3, second member 70 is located relative to first member 40 to position coupling mechanism 90 at the distal ends of slots 80, 81 with engaging member 76 displaced proximally from receiving portion 214*b* of anchor 214. Second member 70 can then be moved distally about coupling mechanism 90 so that coupling mechanism 90 and first member 40 translate proximally along slots 80, 81 to position engaging member 76 on receiver portion 214*b* of anchor 214, as shown in FIG. 1.

Alternatively, engaging member 76 can first be engaged to receiver portion 214*b* of anchor 214 with foot 60 of first member 40 displaced from receiver portion 212*b* of anchor 212 and coupling mechanism 90 located more toward the proximal ends of slots 80, 81. First member 40 can then be translated distally along slots 80, 81 and longitudinally along second member 70 to position foot 60 in engagement with receiver portion 212*b* of anchor 212.

Coupling mechanism 90 maintains first and second members 40, 70 in secured relations to one another while permitting movement relative to one another along a predetermined path defined by slots 80, 81. Coupling mechanism 90 also provides a pivot axis about which first and second members 40, 70 pivot in order to manipulate anchors 212, 214 and/or the bony structure to which each is engaged. The pivot axis location of coupling mechanism 90 varies along slots 80, 81 depending on the relative elevations and separation of foot 60 and engaging member 76 and the relative angle formed between elongated body 42 and shaft 72. The ability to change the pivotal coupling location by translating first member 40 along slots 80, 81 and the longitudinal axis 82 of second member 70 provides an infinite number of pivot axis locations along slots 80, 81. This allows surgical instrument 30 to be adapted to optimally fit in the proximal opening of minimally invasive access portal 200 or other access location into the patient while maintaining the ability to manipulate surgical instrument 30 to deliver forces to the vertebrae.

Coupling mechanism 90 in one embodiment is a rivet-type element with non-removable end members 94, 96. In other embodiments, one or more of end members 94, 96 is removable to facilitate disassembly of first and second members 40, 70.

Figure 2B:
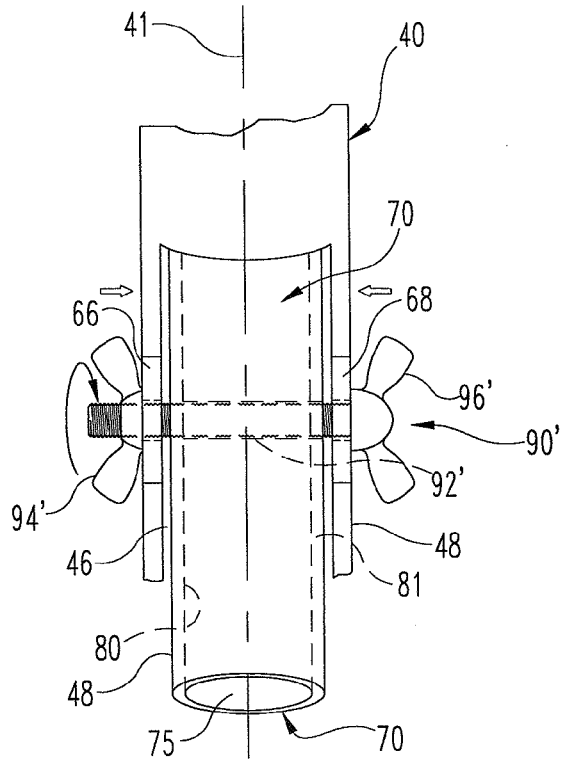
FIG. 2B is an elevation view of another embodiment coupling mechanism.

Another embodiment coupling mechanism 90' is shown in FIG. 2B. Coupling mechanism 90' includes a linking member 92' extending through slots 80, 81 of second member 70 and mounting portions 66, 68 of first member 40. Coupling mechanism 90' also includes a first locking member 94' at one end of linking member 92' located adjacent to mounting portion 66, and an opposite second locking member 96' at the opposite end of linking member 92' adjacent to mounting portion 68. At least one of the locking members 94', 96' is movable along linking member 92' toward and away from its adjacent mounting portion 66, 68. The at least one locking member 94', 96' is moved toward its adjacent mounting portion 66, 68 to clampingly lock second member 70 between mounting portions 66, 68 and secure first member 40 in position in slots 80, 81. In one embodiment, the engagement with locking members 94', 96' prevents any movement of first and second members 40, 70 relative to one another unless coupling mechanism 90' is loosened to permit such movement. In another embodiment, the engagement with locking members 94', 96' prevents any movement of first member 40 along slots 80, 81, but allows pivoting of first and second members 40, 70 relative to one another when sufficient manual force is applied to overcome frictional forces resisting such pivoting movement.

Various embodiments of locking member 94', 96' and linking member 92' are contemplated. In one embodiment, linking member 92' is a threaded shaft and locking member 94', 96' are wing nuts, threaded clamps, or the like, at least one of which is threadingly engaged to the threaded shaft. In another embodiment, linking member 92' is a non-threaded shaft and locking members 94', 96' are secured to linking member 92' with a bayonet lock, clamping lock, crimp, interference fit, weld or other suitable arrangement. For embodiments where linking member 92' extends through passage 75, it is contemplated that linking member 92' can be removed so that an instrument, engaging element other part of construct 210 can be delivered to anchor 214 through passage 75.

In the illustrated embodiments of FIGS. 1 and 3-6, first and second members 40, 70 are coupled to one another with coupling mechanism 90 prior to insertion of surgical instrument 30 in portal 200. First and second members 40, 70 are pivoted to a low profile, nested arrangement such as shown in FIG. 5 where the spacing between foot 60 and engaging member 76 is minimized. Coupling mechanism 90 allows first member 40 to be moved along slots 80, 81 of second member 70 for re-positioning of first and second members 40, 70 relative one another and to allow the surgeon to place foot 60 against anchor 212 and engaging member 76 about anchor 214. When first and second member 40, 70 are mounted to anchors 212, 214, coupling mechanism 90 maintains first and second members 40, 70 in the desired position along slots 80, 81 and provides a pivot axis about which first and second members 40, 70 are pivoted to deliver a compression force to anchors 212, 214 with first and second members 40, 70. Manual force applied to the proximal ends of first and second members 40, 70 pivot first and second members 40, 70 about coupling mechanism 90 to deliver the force with foot 60 and engaging member 76 against anchors 212, 214.

Figure 4:
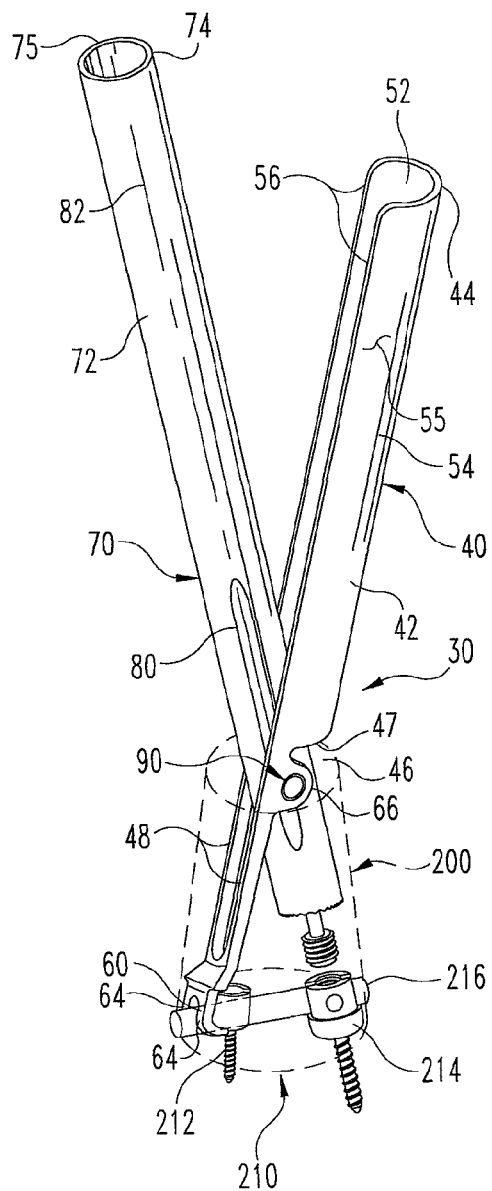
FIG. 4 is a view showing the first and second members of the instrument system in the portal and the distal portion of the second member hidden to show an engaging element being positioned through the second member for engagement to the second anchor.

In one example of use of surgical instrument 30, access portal 200 is positioned to provide access to the spinal column. Procedures can be performed in disc space 208 or on vertebrae 204, 206. Such procedures can include one or more of a discectomy, facectomy, laminectomy, artificial disc placement, fusion device placement, annulus repair or augmentation, or any other spinal surgical procedure. Anchors 212 and 214 can be engaged to respective ones of the vertebrae using any known instruments and techniques. Connecting member 216 can be positioned through access portal 200 and into the receiver portions 212b, 214b of anchors 212, 214. As shown in FIGS. 1 and 6, first member 40 is positioned against receiver portion 212b of anchor 212 while second member 70 is positioned for engagement with anchor 214, as shown in FIGS. 1 and 6. Connecting member 216 is tightly secured to one of the anchors, such as anchor 214, with engaging element 218 in the form of a plug or set screw, for example, delivered through passage 75 of second member 70 to engage receiver portion 214b, as shown in FIG. 4. Engaging element 218 can be an internally or externally threaded set screw, nut, washer, cap or any other device or combination of devices capable of engaging the connecting member 216 in, on, about or adjacent to the receiver portion 214b of anchor 214. A second engaging element can also be positioned in or on receiver portion 212b of the other anchor 212 to loosely retain connecting member 216 therein.

For embodiments in which instrument 30 is employed for distraction, the orientation of foot 60 and toes 64 can be reversed so that foot 60 is offset from arms 40 toward engaging member 76 at the distal end of second member 70, and toes 64 extend away from the distal end of second member 70. This allows foot 60 to be positioned along the side of anchor 212 facing anchor 214 so that when the proximal ends of first and second members 40, 70 are moved away from one another foot 60 and engaging member 76 move away from one another to apply distraction forces between anchors 212, 214.

Connecting member 216 is received in recesses 62, 84 of foot 60 and engaging member 76 of first and second members 40 and 70, respectively, when first member 40 and second member 70 are fully seated on the respective anchors 212, 214. Recesses 62, 84 allow foot 60 and engaging member 76 to be seated further distally on the receiver portions 212b, 214b of anchors 212, 214, providing a firm grip about the anchor to maintain engagement during compression of the spinal column while allowing connecting member 216 to be received through space 62 and recess 84. Second member 70 can further function as reducing instrument to seat connecting member 216 in or on anchor 214 as engaging member 76 is positioned over or on receiver portion 214b. Second member 70 provides a counter-torque as engaging element 218 is tightened in receiver portion 214b against connecting member 216 since the proximal end of shaft 72 can be grasped to prevent receiver portion 214b and/or bone engaging portion 214a of anchor 214 from rotating as engaging element 218 is tightened into position in receiver portion 214b. First and second members 40, 70 are then manipulated relative to one another to deliver a force to vertebrae 204, 206 through anchors 212, 214. Coupling mechanism maintains contact and alignment between first and second members 40, 70 before, during and after compression of the spinal column.

In the illustrated embodiment, second member 70 is received through opening 46 of first member 40 such that shaft 72 and body 42/arms 48 cross one another. Thus, the longitudinal axes 82, 41 of second member 70 and first member 40 form an X-shape in their engaged positions with anchors 212, 214. Side slots 80, 81 of elongated shaft 72 of second member 70 are positioned in alignment with respective ones of mounting portions 66, 68 extending from arms 48, and channel 52 is oriented toward elongated shaft 72 of second member 70. To compress vertebrae 204, 206, the proximal ends 44, 74 of first and second members 40, 70 are moved toward one another. First member 40 and second member 70 pivot relative about the pivot axis provided by coupling mechanism 90. The location along axis 82 of elongated shaft 72 to which first member 40 is engaged to effect pivoting of first and second members 40, 70 can vary infinitely proximally and distally along slots 80, 81 of shaft 72. The location of the pivot axis of coupling mechanism 90 along slots 80, 81 can vary depending on the separation distance of anchors 212, 214, the alignment between vertebrae 204, 206 and anchors 212, 214, the orientation of portal 200 relative to vertebrae 204, 206, and the orientation of first and second members 40, 70 relative to one another and to anchors 212, 214, for example. Accordingly, surgical instrument 30 has application even when anchors 212, 214 are not aligned with another or are spaced various distances from one another while still minimizing the footprint of instrument 30 through portal 200. As proximal ends 44, 74 are moved toward one another, the distal ends of first and second members 40, 70 move toward one another, compressing vertebrae 204, 206 as shown in FIG. 6.

As first and second members 40, 70 are moved toward one another, channel 52 of first member 40 receives elongated shaft 72 of second member 70, as shown in FIG. 5. This nesting arrangement provides a low profile footprint for surgical instrument 30 through portal 200, allowing the size of portal 200 to be minimized, particularly at its proximal opening. Furthermore, receipt of second member 70 through opening 46 of first member 40 provides a low profile footprint extending transversely to connecting member 216 since the longitudinal axes 42, 82 of first and second members 40, 70 are aligned along the axis of connecting member 216 extending between the receiver portions 212b, 214b of anchors 212, 214.

With connecting member 216 secured tightly in anchor 214, anchor member 212 moves along connecting member 216 and toward anchor 214 as the vertebrae are compressed. When the desired compression has been obtained, another engaging element that is provisionally engaged to anchor 212, or that is delivered to anchor 212, can be tightened with a driver instrument to secure anchor 212 with connecting member 216. When secured to anchors 212, 214, connecting member 216 can post-operatively maintain the compression applied with surgical instrument 30. First and second members 40, 70 can then be unmounted from anchors 212, 214 and pivoted to a low-profile orientation such as shown in FIG. 5 and removed through portal 200 while engaged to one another with coupling mechanism 90. Alternatively, first and second members 40, 70 can be removed individually after removing coupling mechanism 90.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A spinal surgical instrument, comprising:
    a first member engageable to a first vertebra, said first member including an elongated body extending along a first longitudinal axis between a proximal end and a distal end, said body further including:
        a proximal portion extending distally from said proximal end to an intermediate end surface;
        a pair of arms extending distally from said intermediate end surface to a foot at said distal end of said body, said pair of arms defining an elongated opening therebetween that extends between said intermediate end surface and said foot, said pair of arms further each including a mounting portion with at least a portion of at least one coupling mechanism mounted to said mounting portions, wherein said foot includes a wall connecting said pair of arms that is laterally offset from a distal projection of said pair of arms, said foot further including a pair of toes extending distally from said wall, said pair of toes each including a proximal portion extending distally from said wall along said first longitudinal axis to a distal portion that extends in a transverse orientation to said proximal portion; and
    a second member including an elongated shaft defining a central passage along a second longitudinal axis that extends between a proximal end and a distal end of said shaft, said distal end of said second member being engageable to a second vertebra, said second member being positioned through said opening between said arms of said first member, said second member including:
        first and second elongated slots extending along said second longitudinal axis on opposite sides of said shaft, said slots opening into said passage at a location between said proximal and distal ends of said shaft, wherein said at least one coupling mechanism on said mounting portions of said first member is received in said slots of said second member, said at least one coupling mechanism securing said first member to said second member in movable relation to one another so that said first member is translatable along said elongated slots of said second member to a selected position of said first member along said second member, said coupling mechanism further providing a pivot axis at said selected position about which said first and second members are pivotal relative one another.

2. The instrument of claim 1, wherein movement of said proximal ends of said first member and said second member toward one another moves said foot of said first member and said distal end of said second member toward one another about said fastener.

3. The instrument of claim 1, wherein said passage of said second member opens at said distal end and said proximal end of said second member.

4. The instrument of claim 1, wherein said proximal portion of said elongated body of said first member includes a channel that is concavely curved between opposite sides of said proximal portion, wherein said channel is linear from said proximal end to said intermediate end surface.

5. The instrument of claim 1, wherein said mounting portions of said first member each project outwardly from a corresponding one of said pair of arms.

6. The instrument of claim 1, wherein said at least one coupling mechanism is movable along said first and second slots of said second member to an infinite number of selectable positions along said first and second slots.

7. The instrument of claim 1, wherein said at least one coupling mechanism includes first and second coupling mechanisms mounted to respective ones of said first and second mounting portions, each of said coupling mechanisms extending through a respective one of said first and second elongated slots of said second member.

8. The instrument of claim 7, wherein each of said coupling mechanisms includes:
    a link member extending through said respective mounting portion and elongated slot;
    a first end member adjacent said respective mounting portion; and
    a second end member within said second member adjacent said respective elongate slot, said first and second end members preventing said link member from being pulled through said respective mounting portion and said respective elongated slot.

9. The instrument of claim 1, further comprising:
    a construct including an elongated connecting member positionable between the first and second vertebrae and first and second anchors for engaging the connecting member to respective ones of the first and second vertebrae, wherein said foot of said first member and said distal end of said second member are mountable to respective ones of the first and second anchors with said connecting member extending between said first and second anchors.

10. The instrument of claim 9, wherein:
    said first anchor include a receiver portion and a bone engaging portion extending distally from said receiver portion, and said distal portions of said pair of toes extend along a distal facing side of said receiver portion on opposite sides of said bone engaging portion and said proximal portions of said pair of toes extend along said receiver portion in complementary engagement with said receiver portion.

11. The instrument of claim 10, wherein said pair of toes is separated by a space and said connecting member extends from said receiver portion of said first anchor into said space.

12. A spinal surgical instrument, comprising:
    a first member including an elongated body extending along a first longitudinal axis between a proximal end and a distal end, said body including a proximal portion extending from said proximal end that defines a handle portion and a distal portion that includes a pair of arms spaced from one another on opposite sides of an opening between said pair of arms, said pair of arms extending distally from said handle portion to a foot at said distal end of said first member, said opening extending between said foot and said proximal handle portion, said pair of arms further including at least one coupling mechanism mounted thereto; and
    a second member including an elongated shaft that extends along a second longitudinal axis and defines a passage extending between and opening at a proximal end and a distal end of said elongated shaft, said second member being movably received in said opening of said first member with said elongated shaft including opposite slots elongated along said second longitudinal axis for receiving said at least one coupling mechanism of said first member, said at least one coupling mechanism being movable along said slots in the direction of said second longitudinal axis of said second member to select an axial position of said first member relative to said second member, said at least one coupling mechanism securing said first member and said second member to one another to maintain said selected axial position while permitting said distal ends of said first and second members to move toward and away from one another by pivoting said first and second members about a pivot axis provided by said at least one coupling mechanism at said selected axial position;

wherein said distal end of said first member includes said foot extending between said pair of arms, said foot including a wall extending between said pair of arms, wherein said wall is offset laterally from a distal projection of said pair of arms, wherein said distal end of said first member further includes a pair of toes each including a first portion extending distally from said wall and a second portion extending from a distal end of said first portion and transversely to said first portion.

13. The instrument of claim 12, wherein said second portions of said toes define an open space therebetween.

14. The instrument of claim 12, wherein said coupling mechanism is positionable at an infinite number of positions along said pair of slots.

15. The instrument of claim 12, wherein said pair of slots open into said passage of said second member and a portion of said at least one coupling mechanism is located in said passage to secure said first member to said second member while maintaining said passage in a substantially unobstructed condition from said proximal end to said distal end thereof.

16. The instrument of claim 12, wherein said elongated body of said first member includes a concavely curved channel extending at least partially between said proximal end and distal ends thereof, where said channel is oriented toward said elongated shaft of said second member, said channel being sized to receive said shaft of said second member therein when said first and second members are pivoted relative to one another to substantially align said first and second longitudinal axes relative to one another.

17. A spinal surgical method, comprising:
positioning a minimally invasive access portal in a patient to provide a protected pathway to at least one vertebra;
engaging first and second anchors to the at least one vertebra;
positioning a distal end of a first member and a distal end of a second member into the portal, the first member including an elongated body extending from the distal end of the first member to an opposite proximal end of the first member with the first member defining an opening extending through the body thereof between the proximal and distal ends, wherein the second member extends from the distal end of the second member through the opening of the first member to an opposite proximal end of the second member, wherein said distal end of said first member includes said foot extending between said pair of arms, said foot including a wall extending between said pair of arms, wherein said wall is offset laterally from a distal projection of said pair of arms, wherein said distal end of said first member further includes a pair of toes each including a first portion extending distally from said wall and a second portion extending from a distal end of said first portion and transversely to said first portion;
axially translating the first and second members relative to one another along a predetermined path defined by the second member to select a position of the first member along the second member to mount the distal end of the first member to the first anchor and the distal end of the second member to the second anchor; and
axially fixing the first and second members to one another at the position and pivoting the first member and the second member about a pivot axis defined at the position to move the distal ends of the first and second members relative to one another to deliver a force to the first and second anchors with the first and second members.

18. The method of claim 17, further comprising locking the first and second anchors in position relative to one another while maintaining the force applied between the first and second anchors with the first and second members.

19. The method of claim 17, wherein:
the second member includes a shaft with a passage extending between and opening at the proximal and distal ends thereof, the shaft including a pair of slots located in opposite sides thereof that open into the passage; and
the first member includes a pair of mounting portions on opposite sides of the openings and a pair of coupling mechanisms extending through the mounting portions and the pair of slots to couple the first and second members to one another.

* * * * *